(12) United States Patent
Schwarzer et al.

(10) Patent No.: US 8,029,845 B2
(45) Date of Patent: Oct. 4, 2011

(54) COMPOSITIONS OF SUGAR-CONTAINING STEROL SOLIDS DISPERSIONS

(75) Inventors: Joerg Schwarzer, Hilden (DE); Robert Salacz, Senden (DE); Peter Horlacher, Illertissen (DE); Manuela Kraus, Illertissen (DE); Wolfgang Albiez, Illertissen (DE)

(73) Assignee: Cognis IP Management GmbH, Duesseldorf (DE)

( * ) Notice: Subject to any disclaimer, the term of this patent is extended or adjusted under 35 U.S.C. 154(b) by 973 days.

(21) Appl. No.: 11/360,160

(22) Filed: Feb. 23, 2006

(65) Prior Publication Data

US 2006/0204630 A1   Sep. 14, 2006

(30) Foreign Application Priority Data

Feb. 24, 2005 (DE) .................... 10 2005 008 445

(51) Int. Cl.
  *A23L 1/236* (2006.01)
(52) U.S. Cl. ............ 426/548; 127/29; 127/30; 426/442; 426/531; 426/601; 426/658; 514/169
(58) Field of Classification Search .............. 426/601, 426/442, 531, 548, 658; 514/169; 424/238; 127/29, 30
See application file for complete search history.

(56) References Cited

U.S. PATENT DOCUMENTS

| | | | |
|---|---|---|---|
| 3,881,005 A | 4/1975 | Thakkar et al. | |
| 4,195,084 A | 3/1980 | Ong | |
| 5,502,045 A | 3/1996 | Miettinen et al. | |
| 6,376,482 B2 | 4/2002 | Akashe et al. | |
| 6,623,780 B1 | 9/2003 | Stevens et al. | |
| 6,627,245 B1 | 9/2003 | Doat et al. | |
| 2003/0180369 A1* | 9/2003 | Grisoni ..................... | 424/490 |
| 2006/0035871 A1 | 2/2006 | Auweter et al. | |

FOREIGN PATENT DOCUMENTS

| | | |
|---|---|---|
| DE | 102 53 111 A1 | 5/2004 |
| EP | 0 897 671 B1 | 2/1999 |
| EP | 0 947 197 A1 | 10/1999 |
| EP | 1 059 851 A1 | 12/2000 |
| EP | 1 059 851 B1 | 12/2000 |
| EP | 1 074 185 A1 | 2/2001 |
| EP | 1 142 494 A1 | 10/2001 |
| EP | 1 275 309 A1 | 1/2003 |
| GB | 934686 | 8/1963 |
| WO | WO 98/13023 A1 | 4/1998 |
| WO | WO 99/39715 A1 | 8/1999 |
| WO | WO 99/59421 A1 | 11/1999 |
| WO | WO 99/44442 A1 | 12/1999 |
| WO | WO 99/63841 A1 | 12/1999 |
| WO | WO 01/32036 A1 | 5/2001 |
| WO | WO 02/28204 A1 | 4/2002 |
| WO | WO 03/105611 A2 | 12/2003 |

* cited by examiner

*Primary Examiner* — Brent O Hern
(74) *Attorney, Agent, or Firm* — Diehl Servilla LLC

(57) ABSTRACT

The invention relates to solids dispersions in the form of a solid solution containing a) at least about 0.1% by weight of sterols and/or stanols and/or esters thereof, and b) at least about 50% by weight of sugars and/or sugar alcohols, based on the total weight of the solids dispersion. These solids dispersions provide for simple further processing of the hydrophobic sterols and stanols, and sterol or stanol esters, through improved dispersion behavior in foods, and are distinguished by excellent stability upon storage.

12 Claims, No Drawings

COMPOSITIONS OF SUGAR-CONTAINING STEROL SOLIDS DISPERSIONS

CROSS-REFERENCE TO RELATED APPLICATIONS

This application claims priority from DE 102005008445.1 filed Feb. 24, 2005, the entire contents of which are incorporated herein by reference.

FIELD OF THE INVENTION

This invention relates generally to foods and, more particularly, to compositions containing sterols, stanols and/or esters thereof for incorporation in foods, cosmetic and pharmaceutical preparations, to a process for their production and to preparations, more particularly foods, which contain these compositions.

BACKGROUND OF THE INVENTION

Phytosterols and their derivatives hardened by hydrogenation, phytostanols, have been known for many years for their cholesterol-lowering properties. As early as 1991, researchers demonstrated the effectiveness of these substances in inhibiting the absorption of cholesterol in the intestine and through the inner blood vessel walls. Accordingly, sterols and stanols are widely used in the food industry because, through their hypocholesterolemic effect, they minimize future diseases, such as atherosclerosis, heart disease and hypertension. Since phytosterols and stanols are insoluble in water and only poorly soluble in fats and oils, the incorporation of these cholesterol-lowering agents in food preparations, cosmetic or pharmaceutical products poses considerable problems. The unfavorable solubility behavior of the substances results not only in poor dispersibility, but also in reduced bioavailability and in unsatisfactory stability of the food preparations.

Efforts to solve this problem have included the formulation of esters of the sterols, as described in European patent application EP 1275309 A1, or esters of the stanols, as described in U.S. Pat. No. 5,502,045, which had slightly improved processability through their better solubility, but which also showed different hypocholesterolemic activity in relation to the free sterols. However, the esterified derivatives are also not sufficiently soluble to allow simple incorporation.

Numerous patent applications describe how the availability of sterols can be improved by reducing their particle sizes, mainly by micronization. Thus, DE 102 53 111 A1 describes powder-form phytosterol formulations with a mean particle size of 0.01 to 100 μm which are readily redispersible in water. A process for the production of a sterol dispersion, in which the sterols have a particle size distribution of 0.1 to 30 μm, is disclosed in International patent application WO 03/105611 A2.

However, the micronization of the sterol particles is not in itself sufficient to enable satisfactory incorporation into food products. Although the bioavailability of the finely dispersed particles can be improved by increasing the surface area, the micronized particles show poor wetting behavior, readily aggregate, and generally float on the surfaces of aqueous dispersions. In many cases, the ground sterol can only be dispersed in a beverage by special methods involving intensive mixing. However, intensive mixers are not normally available to the end user of the food manufacturers.

Accordingly, many manufacturers combine micronization of the sterols with the additional use of emulsifiers. One example of this are the preparations described in European patent EP 0897671 B1 which contain sterols and sterol esters with a particle size of at most 15 μm in a mixture with emulsifiers, the ratio by weight of emulsifier to sterol in the aqueous phase being less than 1:2. A sterol/emulsifier dispersion disclosed in European patent application EP 1142494 A1 has a particle size distribution of 1 to 40 μm. Commonly used emulsifiers are monoglycerides and polysorbates as disclosed in U.S. Pat. No. 6,623,780 B1, U.S. Pat. No. 6,376,482 B2, WO 02/28204 A1. Even though these emulsifiers are distinguished by high compatibility and have been known for some time as food emulsifiers, efforts are being made to reduce the quantity in which such emulsifiers are used or even to avoid them altogether because emulsifiers also influence the bioavailability of other substances present in the foods or can adversely affect the stability of the formulations.

Avoiding emulsifiers was also the goal of the sterol formulations disclosed in European patent EP 1059851 B1 which contain thickeners for better dispersibility.

Numerous other methods for improving solubility and dispersibility, such as formulating as emulsions, microemulsions, dispersions, suspensions or complexing with cyclodextrins or bile salts, are described in International patent application WO 99/63841 A1, which also mentions formulation in the form of solids dispersions. PEG, PVP, copolymers, cellulose ethers and esters are proposed as carriers.

European patent application EP 1074185 A1 also describes sterol-containing formulations with a matrix which are distinguished by advantageous organoleptic properties of the preparations and which are used for confectionery. However, these formulations are prepared with the addition of water or water and emulsifiers and, accordingly, show reduced stability.

The problem addressed by the present invention was to provide a formulation which would allow the simple and effective dispersion and incorporation of sterols, stanols and esters thereof in foods while reducing or avoiding the use of emulsifiers. The sterol formulation would be readily produced and would be distinguished by high stability in storage.

BRIEF SUMMARY OF THE INVENTION

The present invention relates to solids dispersions in the form of a solid solution comprising
a) at least about 0.1% by weight of a sterol or of a stanol, or esters thereof, and mixtures thereof; and
b) at least about 50% by weight of a sugar or of a sugar alcohol and mixtures thereof,
based on the total weight of the solids dispersion.

The solids dispersions according to the invention are distinguished by good solubilizing properties, reduced aggregation and agglomeration properties and improved wettability, and thus enable sterols, stanols and esters thereof to be readily dispersed in water- and fat-containing preparations. They have excellent handling behavior because they are available in various particle sizes and can be further processed without complicated treatment and, in addition, show high stability in storage.

The solids dispersions with the above composition in the form of solid solutions of the present invention may readily be incorporated into foods, more particularly in milk, milk beverages, whey and yoghurt beverages, margarine, fruit juices, fruit juice mixtures, fruit juice beverages, vegetable juices, carbonated and still beverages, soya milk beverages or high-protein liquid food substitute beverages and fermented milk preparations, yoghurt, drinking yoghurt or cheese preparations, and in cosmetic or pharmaceutical preparations.

Accordingly, the present invention relates to preparations which contain solids dispersions of the composition described above. They are preferably used in beverages and milk products which then contain from about 0.1 to 50% by weight and preferably from about 1 to 20% by weight of the solids dispersions, based on the total weight of the food.

DETAILED DESCRIPTION OF THE INVENTION

Sterols, Stanols and Esters Thereof

Sterols obtained from plants and vegetable raw materials, so-called phytosterols and phytostanols, and esters of the phytosterols and esters of the phytostanols are used for the purposes of the invention. Known examples are ergosterol, brassica sterol, campesterol, desmosterol, clionasterol, stigmasterol, poriferasterol, chalinosterol, sitosterol and mixtures thereof. Of these, β-sitosterol and campesterol are preferably used. The hydrogenated saturated forms of the sterols, so-called stanols, are also included among the compounds used, β-sitostanol and campestanol likewise being preferred. In addition, esters of the phytosterols and esters of the phytostanols are used in the formulations according to the invention. These derivatives of the sterols and stanols are also not sufficiently hydrophilic and wettable to be readily incorporated into foods or other preparations. Esterification products with saturated and/or unsaturated $C_{6-22}$, and preferably $C_{12-18}$ fatty acids, are preferably used, although the invention is not limited to esters of this type. However, unesterified sterols, which contain small quantities of stanols from their production, are particularly preferred.

Sugars and Sugar Alcohols

The compounds used as sugars all contain food-grade sugars selected from the group consisting of glucose, sucrose, fructose, trehalose, maltose, maltodextrin, cyclodextrin, invert sugar, palatinose and lactose and mixtures thereof. Glucose or sucrose are preferred. The sugar alcohols used in the present invention are toxicologically safe and food-compatible. Sugar alcohols selected from the group consisting of sorbitol, D-mannitol, maltitol, lactitol, isomalt and xylitol, and mixtures thereof, may be used, sorbitol being particularly preferred. Suitable quantities for the sugars and/or sugar alcohols in the solids dispersions according to the invention are at least about 50% by weight, based on the total weight of the solids dispersion, preferably at least 80% by weight and more particularly at least about 90% by weight.

Solids Dispersions in the Form of Solid Solutions and their Production

The solids dispersions according to the invention in the form of solid solutions are solutions of solids in solids by which very fine distribution of sterols, stanols or esters thereof in the sugar and/or sugar alcohol is accomplished since the sterols are embedded in a matrix. The distribution of the disperse phase may be coarsely disperse, colloidally disperse or molecularly disperse. Solids dispersions in the form of solid solutions are water-free, containing less than about 0.5% by weight, preferably less than about 0.3% by weight and more particularly less than about 0.1% by weight of water.

These formulations differ clearly in their physicochemical behavior from simple powder mixtures obtained by mixing fine powders, as described, for example, in Example 3 of International patent application WO 98/13023, which still represent two physically separated components. In the solids dispersions according to the invention, the sterols, stanols and esters thereof are advantageously embedded in a matrix, even with a comparable narrow particle size distribution.

European patent application EP 1074185 A1 also describes sterol-containing formulations with a matrix which are distinguished by advantageous organoleptic properties of the preparations and which are used for confectionery. However, these formulations are prepared with the addition of water or water and emulsifiers and, hence, do not represent a typical solids dispersion.

In contrast to the physical powder mixtures and water-containing matrix systems, the solids dispersions according to the invention are distinguished by high storage stability, excellent solubilizing properties, reduced aggregation and agglomeration properties, and improved wettability.

Basically, solids dispersions can be produced by a melting or dissolving method. In view of the different solubility properties of sugars and sterols, the present solids dispersions are preferably produced by the melting method, in which the sterols, stanols and/or their esters are melted together with the sugars and/or sugar alcohols. The resulting melt solidifies on cooling. The melt can be cooled while stirring or mixing. Simultaneous extrusion is also possible. Under the effect of shear forces, the melt is warm as it issues from the extruder and is then cooled, for example on cooling belts.

The solids dispersions according to the invention in the form of solid solutions are obtainable by
a) melting sterols and/or stanols and/or esters thereof together with a sugar and/or sugar alcohol at temperatures of from about 60 to 190° C. and
b) cooling the melt to ambient temperature.

The solidified melt may then optionally be size-reduced to the desired particle size.

The components are melted without the addition of water. The melt formed is kept at the temperature of from about 60 to 190° C., preferably at about 100 to 190° C. and more particularly at about 120 to 180° C. until the components have completely melted.

The solids dispersions according to the invention in the form of solid solutions can be obtained by
a) melting at least about 0.1% by weight (based on the total weight of the final formulation) of sterols and/or stanols and/or esters thereof together with at least about 50% by weight (based on the total weight of the final formulation) of sugar and/or sugar alcohol at temperatures of from about 60 to 190° C.,
b) cooling the melt to ambient temperature and
c) optionally size-reducing the solidified melt by grinding to a mean particle size of about 125 μm or larger.

Particle Size Distribution

The particle size of the untreated sterols before the production of the solids dispersions is not crucial to the final formulation, which considerably simplifies processing. Flakes, prills, briquettes or even blocks can be used because the product is melted with sugar.

After solidification of the solids dispersions, the formulations may be ground to the desired particle size using conventional size-reducing machines. The solids dispersions do not have to be micronized because, even with particle size distributions of about 125 to 500 μm, the embedded sterol particles are present in micronized form after dissolution of the sugar or sugar alcohol. Formulations in the form of flakes, prills, briquettes or blocks may be suitable in the interests of simple further processing. Particle sizes of 125 μm, 250 μm and 500 μm can be obtained by adjusting the grinding for the solids dispersions. The larger the particle size of the solids dispersions then, the easier the powder could be handled. Powders with a mean particle size of from about 125 μm to 4,000 μm (as measured by sieve analysis to the standards of the European Pharmacopoeia (EuAB): main fraction of sieving with sieve mesh widths of 90, 125, 250, 500, 1,000 and 4,000 μm) are preferred, powders with a mean particle size of from about 250 μm to 1,000 μm more particularly preferred, and powders with particle sizes of from about 250 to 500 μm are most particularly preferred.

Formulations for Sugar-Containing Solids Dispersions

Compositions according to the invention include, but are not limited to, the following, and shall be understood to include "mixtures thereof" of the components a) and b), respectively:

A) Solids dispersions in the form of solid solutions containing
    a) at least about 0.1% by weight sterols and/or stanols and/or esters thereof; and
    b) at least about 50% by weight sugars and/or sugar alcohols, based on the total weight of the solids dispersion.

B) Solids dispersions in the form of solid solutions containing
    a) at least about 1% by weight sterols and/or stanols and/or esters thereof; and
    b) at least about 80% by weight sugars and/or sugar alcohols, based on the total weight of the solids dispersion.

By virtue of their improved storage stability, dispersibility and processability in foods, the following solids dispersion formulations are preferred:

C) Solids dispersions in the form of solid solutions containing
    a) at least about 3% by weight sterols and/or stanols and/or esters thereof; and
    b) at least about 90% by weight sugars and/or sugar alcohols, based on the total weight of the solids dispersion.

D) Solids dispersions in the form of solid solutions containing
    a) at least about 1% by weight sterols and/or stanols and/or esters thereof;
    b) at least about 80% by weight sugars and/or sugar alcohols; and
    c) less than about 0.5% by weight water, based on the total weight of the solids dispersion.

E) Solids dispersions in the form of solid solutions containing
    a) at least about 0.1% by weight sterols and/or stanols and/or esters thereof; and
    b) at least about 50% by weight sugar alcohols, based on the total weight of the solids dispersion.

Solids dispersions having the following composition are particularly preferred:

F) Solids dispersions in the form of solid solutions containing
    a) at least about 1% by weight sterols and/or stanols and/or esters thereof; and
    b) at least about 80% by weight sugar alcohols, based on the total weight of the solids dispersion.

G) Solids dispersions in the form of solid solutions containing
    a) at least about 1% by weight sterols and/or stanols and/or esters thereof;
    b) at least about 80% by weight sugars and/or sugar alcohols; and
    c) less than about 0.3% by weight water, based on the total weight of the solids dispersion.

H) Solids dispersions in the form of solid solutions containing
    a) at least about 3% by weight sterols and/or stanols and/or esters thereof;
    b) at least about 90% by weight sugars and/or sugar alcohols; and
    c) less than about 0.5% by weight water, based on the total weight of the solids dispersion.

Emulsions having the following composition are especially preferred:

I) Solids dispersions in the form of solid solutions containing
    a) at least about 1% by weight sterols and/or stanols and/or esters thereof; and
    b) at least about 50% by weight sorbitol, based on the total weight of the solids dispersion.

J) Solids dispersions in the form of solid solutions containing
    a) at least about 1% by weight sterols and/or stanols and/or esters thereof;
    b) at least about 80% by weight sugars and/or sugar alcohols; and
    c) less than about 0.1% by weight water, based on the total weight of the solids dispersion.

K) Solids dispersions in the form of solid solutions containing
    a) at least about 3% by weight sterols and/or stanols and/or esters thereof;
    b) at least about 90% by weight sugars and/or sugar alcohols; and
    c) less than about 0.3% by weight water.

Formulations with the following composition are particularly stable upon storage:

L) Solids dispersions in the form of solid solutions containing
    a) at least about 3% by weight sterols and/or stanols and/or esters thereof;
    b) at least about 90% by weight sugars and/or sugar alcohols; and
    c) less than about 0.1% by weight water, based on the total weight of the solids dispersion.

The following examples are illustrative of, but not limiting of, the present invention.

EXAMPLES

Example 1

Tests with Sugar—Sucrose 25 g Generol® 122 N in the form of prills with a mean particle size of 500 to 800 μm (Cognis Germany) and 225 g commercial cane sugar—sucrose—were melted together and stirred. The melt was then cooled with manual kneading. The solidified melt was then ground in a standard domestic mill (Moulinette®) to a mean particle size of A: 125 μm and B: 250 μm and C: 500 μm (sieve analysis using a Retsch sieve, main fraction of sieve analysis to EuAB).

Dispersion Test

The powder obtained with a sterol content of 10% by weight was dispersed in orange juice, milk and water by comparison with ground sterols (Generol® 122NG, mean particle size 20-40 μm, as determined by laser diffraction). To this end, 250 ml of the liquid to be tested were poured into a glass beaker and stirred (ca. 100 r.p.m.). Powder (A, B, C and Comparison) was added to the stirred liquid in such a quantity that the dispersion had a sterol content of 0.5%. Dispersion behavior was then evaluated.

|  | Sterol/sugar dispersion | Untreated (Comparison) |
| --- | --- | --- |
| Orange Juice | Good (A, B, C) | Poor |
| Water, cold | Good (A, B, C) | Poor |
| Water, warm | Good (A, B, C) | Poor |
| Milk | Good (A, B, C) | Poor |

The untreated sterol was hydrophobic, and it was not wetted and remained on the surface. The sterol/sugar dispersions A, B and C were thoroughly wetted by the liquid, the sugar in all three formulations dissolved relatively quickly and released the fine-particle sterol in dispersed form. The larger the particle size was, the easier the powder was to handle.

Particle Size Analysis:

The particle sizes of the coarser particles were determined by sieve size analysis (to the EuAB). The following sieve sizes were used (mesh width in μm): 90, 125, 250, 500, 1,000, 4,000. With mean particle sizes below 30 μm, size determination could not be carried out by simple dry sieving. In this case, particle size determination was carried out by laser diffraction. The particle size distribution was determined with a Beckman Coulter LS 230 particle size analyzer (1994 operating instructions). Water was used as the measuring medium.

The particle sizes of the final formulations were measured immediately after preparation of the dispersions. In the test, prills with a particle size of 500 to 800 μm (main fraction of the distribution: sieve analysis to EUAB) were used as starting material for the pure sterols.

Particle size of the ground sterol/sugar solids dispersions: main fraction A: 125 μm and B: 250 μm and C: 500 μm sieve analysis)

Dispersed in water, the maximum of the particle size distribution was at 20-50 μm (as determined by laser diffraction). The sugar thus dissolved in the water and the particle size distribution of the pure sterol particles was measured.

Example 2

Tests with Sugar Alcohols—Sorbitol

With sugar alcohols, particularly sorbitol, a paste-like compound was initially obtained after melting and solidified on cooling. However, this solid can be re-liquefied by heating and, for example, can be added to cold water. The sorbitol dissolves and the sterol is finely dispersed.

Example 2a 25 g unground sterol (Generol® 122 N (Cognis Germany) were melted together with 225 g sorbitol (70%). The melt was then cooled while stirring or kneading (conditions as in Example 1) until it solidified.
Dispersion test of Example 1:
cold water: good
warm water: good
milk: good
orange juice: good Example 2b The test described in Example 2a was repeated with solids dispersion heated to 75° C. This dispersion had paste-like flow behavior.
Result of dispersion test:
cold water: good
warm water: good
milk: good
orange juice: good

What is claimed is:

1. A composition in the form of a solid solution comprising:
    (a) at least about 0.1% by weight of at least one compound selected from the group consisting of sterols, stanols, sterol esters, stanol esters, and mixtures thereof, and
    (b) at least about 50% by weight of at least one compound selected from the group consisting of sugars, sugar alcohols, and mixtures thereof, based on the total weight of the composition,
    wherein said composition is in the form of a solid solution and is prepared by a process comprising the steps of:
        (i) melting components (a) and (b) together, until said components have completely melted, without the addition of water, to form a melt,
        ii) mixing said melt to form a mixed melt,
        iii) cooling said mixed melt to ambient temperature, thereby forming said solid solution, and
        iv) size reducing said solid solution to form particles,
    wherein said particles are wetted and release fine-particle sterol or stanol in dispersed form when mixed with water or a water- or fat-containing preparation.

2. The composition according to claim 1, wherein the size-reduced solid solution has a mean particle size of about 125 μm to about 4000 μm, as measured by sieve analysis.

3. The composition according to claim 2 wherein said mean particle size is about 250 μm to about 500 μm, as measured by sieve analysis.

4. The composition according to claim 1 wherein said sugar is selected from the group consisting of glucose, sucrose, fructose, trehalose, maltose, maltodextrin, cyclodextrin, invert sugar, palatinose, lactose, and mixtures thereof.

5. The composition according to claim 1 wherein said sugar alcohol is selected from the group consisting of sorbitol, D-mannitol, maltitol, lactitol, isomalt, xylitol, and mixtures thereof.

6. The composition according to claim 4 wherein said sugar comprises glucose and/or sucrose.

7. The composition according to claim 5 wherein said sugar alcohol comprises sorbitol.

8. The composition according to claim 1 wherein said sterol comprises β-sitosterol and/or campesterol.

9. The composition according to claim 1 wherein said stanol comprises β-sitostanol and/or campestanol.

10. The composition according to claim 1 which contains less than about 0.1% by weight of water.

11. The composition according to claim 1 wherein component (b) is present in an amount of at least about 80%.

12. A food product comprising the composition of claim 1.

* * * * *